United States Patent [19]

Shaposka et al.

[11] Patent Number: 4,897,138

[45] Date of Patent: Jan. 30, 1990

[54] SEALING OF PLASTIC TUBES

[75] Inventors: John B. Shaposka; Dudley Spencer, both of Wilmington, Del.

[73] Assignee: Denco, Inc., Wilmington, Del.

[21] Appl. No.: 287,461

[22] Filed: Dec. 20, 1988

Related U.S. Application Data

[63] Continuation-in-part of Ser. No. 51,390, May 18, 1987, Pat. No. 4,793,880.

[51] Int. Cl.⁴ .................. B29C 57/10; B29C 65/20
[52] U.S. Cl. ................... 156/158; 156/304.2;
156/304.6; 156/499; 156/503; 156/507;
264/322; 264/DIG. 65; 264/DIG. 66; 425/392;
425/403; 493/308; 604/905
[58] Field of Search .............. 156/158, 304.1, 304.2,
156/304.6, 503, 507, 499; 604/905; 264/209.3,
322, DIG. 65, DIG. 66; 425/392, 403; 228/60

[56] References Cited

U.S. PATENT DOCUMENTS

| | | | |
|---|---|---|---|
| 3,413,175 | 11/1968 | Rochla | 156/499 |
| 3,929,943 | 12/1975 | Klimaszewski, Jr. | 264/322 |
| 4,369,779 | 1/1983 | Spencer | 156/304.2 |
| 4,737,214 | 4/1988 | Leurink et al. | 156/158 |

Primary Examiner—Michael Wityshyn
Attorney, Agent, or Firm—Connolly & Hutz

[57] ABSTRACT

A plastic tube is sealed at its end by placing the tube in a pair of spaced apart tube holders having tube receiving pockets. The tube is cut by a cutting device movable into and out of the space between the pockets to form two distinct tube sections which are melted at their ends while in the clamped condition. The cut ends are then brought into contact with each other in a mis-aligned condition offset by one-half the thickness of a tube wall to seal the tube end.

15 Claims, 2 Drawing Sheets

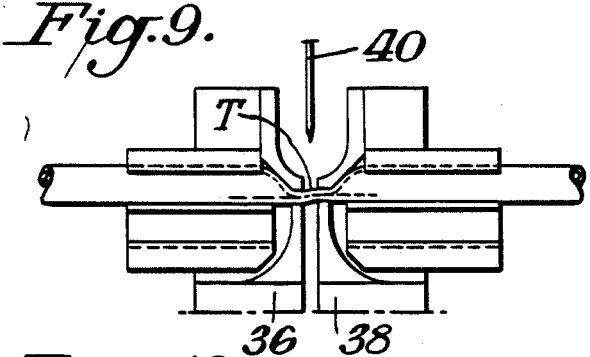
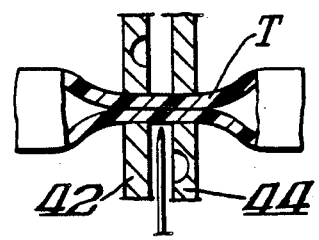
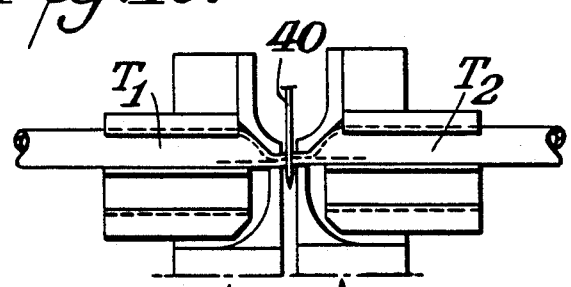
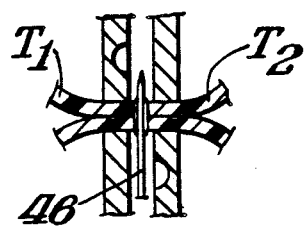
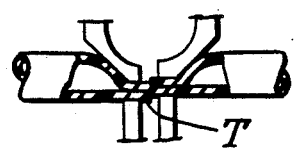
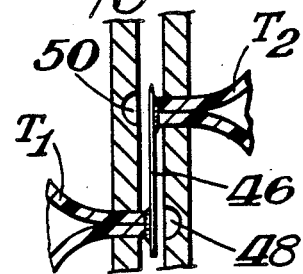
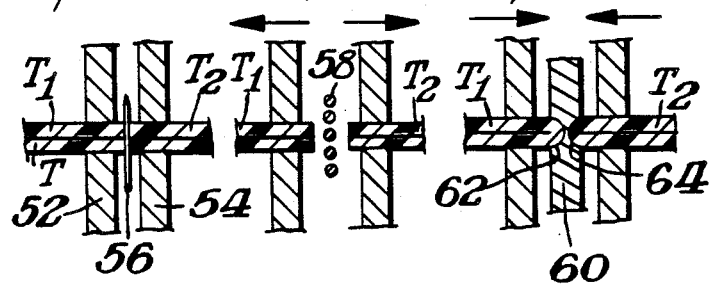
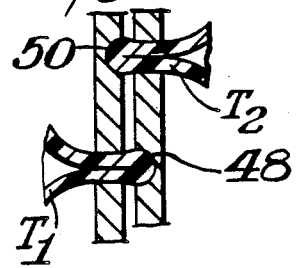

SEALING OF PLASTIC TUBES

CROSS-REFERENCE TO RELATED APPLICATION

This application is a continuation-in-part of application Ser. No. 51,390 filed May 18, 1987, now U.S. Pat. No. 4,793,880.

BACKGROUND OF INVENTION

Parent application Ser. No. 51,390 discloses techniques for the sterile welding of plastic tubes wherein a pair of tubes are placed in pockets or grooves of a pair of spaced apart tube holders. A cutting device, such as a wafer, moves into the space between the tube holders to completely cut through both tubes. The tubes are then off-set from each other and pressed into contact after being heated so that the end of one tube section becomes welded to the end of another tube section.

While the techniques disclosed in parent application serial no. 51,390 are quite effective as a means of connecting one tube section to another tube section, there is sometimes a need to simply seal a tube without joining it to another tube. This need occurs, for example, where a tube is used in a laboratory as a conduit and then after its use it is desired to obtain absolute seal integrity.

SUMMARY OF INVENTION

An object of this invention is to provide an apparatus of the type disclosed in parent application Ser. No. 51,390 wherein a single tube may be sealed in a reliable manner.

In accordance with this invention various alternatives are provided for achieving effective seal integrity wherein a welding procedure is used for a pre-sterilized, pre-sealed stub end of a tube.

In accordance with one embodiment of this invention a single tube is placed in the type of device disclosed in parent application Ser. No. 51,390 and is severed and then heated to melt the ends of the tube sections resulting from the cutting operation. The tube holders are then moved so as to be in slight mis-alignment with each other whereby when the tube sections are brought into contact with each other the wall of one tube section functions to permanently close the other tube section.

In accordance with a further embodiment of this invention the mis-alignment is achieved by having the tube holders initially set in the shifted or mis-aligned condition rather than performing the shifting action after the severing has taken place.

In accordance with still another embodiment of this invention die pockets are provided opposite each end of the tube sections after the tube sections have been shifted completely out of alignment with each other so as to seal the cut ends when the cut ends come in contact with the cold die pockets. A variation of this technique is to maintain the tube sections aligned with but spaced from each other and to insert a die block in the spacing so that the ends of the tube sections are sealed when the tubes are moved into contact with the cold die pockets.

THE DRAWINGS

FIGS. 9-11 are top plan views schematically showing the sequence of operation in accordance with a further embodiment of this invention;

FIG. 12-15 are top plan views schematically showing the sequence of operation of yet another embodiment of this invention; and FIGS. 16-18 are top plan views showing the sequence of operation of still yet another embodiment of this invention.

DETAILED DESCRIPTION

The present invention involves, in general, the sealing of a tube end wherein the tube would be placed in pockets or grooves in a pair of tube holders which are spaced from each other. The tube is severed so as to create a pair of tube sections which are heated to melt their opposing ends and some means is utilized to effectively seal one of the ends as a result of a lateral shifting of the tube section. Any suitable means may be accomplished for performing these steps. The apparatus disclosed in parent application Ser. No. 51,390, the details of which are incorporated herein by reference thereto, is particularly adapted for practicing the invention. In that apparatus, each tube holder includes two grooves or pockets for receiving a pair of tubes. Where the present invention is practiced with that apparatus it is only necessary to use one pocket from each tube holder since only a single tube would be placed in the apparatus. Accordingly, it would also be possible to modify the apparatus of parent application Ser. No. 51,390 by omitting one set of tube holding pockets.

Figure 5:
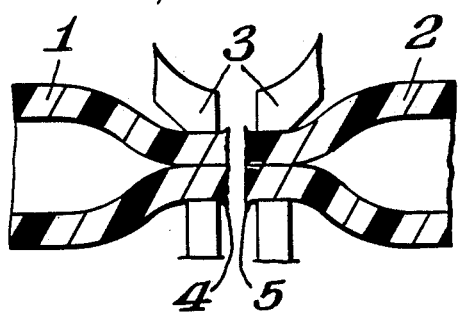
FIGS. 5-7 show the sequence of operation which results from joining tube sections which are not mis-aligned.
Figure 6:
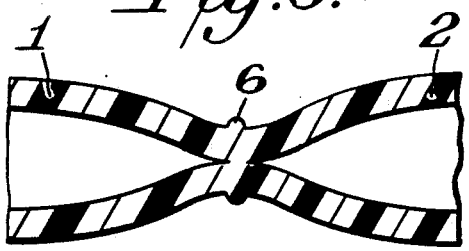
Figure 7:
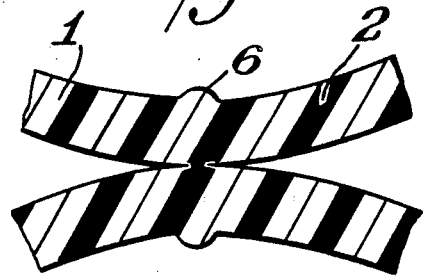

Parent application Ser. No. 51,390 is concerned with the problem of sterily welding two plastic tubes together. Such tubes generally being made of pvc. The present invention differs in that it utilizes the same technology, but is concerned with sealing tubes as well as welding them. With the parent application, during the welding procedure, care is taken to precisely align the molten stub ends of the tube before pressing them together to form the weld. This is illustrated in FIGS. 5-6 wherein the tube sections 1,2 are compressed by clamps 3,3 with the cut ends 4,5 being heated so as to be in a molten condition. (See FIG. 5) The cut ends 4,5 are then pressed together to form the welded connection 6. If the tube alignment is not perfect the tubes are difficult to open. The tack seal holds the tubes in the flat state. As shown in FIG. 7, a thin area of connection exists at the junction of the welded tube sections 1,2. Previously, this has been recognized as a problem. The present invention takes what was previously considered a problem and applies that problem to obtain a distinct benefit, namely, for supplying the need that exists for a device that can make a re-openable seal in a tube wall.

Such a device would have numerous advantages:
 (1) Avoids contamination problems when you want to only temporarily seal off a tube without using a hemostat, etc.

(2) Can be used to separate the reaction components (Epoxy for example) until needed.

(3) Can be used as a "tamper proof seal".

(4) Cheap replacement for a valve.

(5) Minimizes number of fittings required (and also the need to sterilize said fittings).

In addition, since the welder and sealer are the same device, other benefits are seen:

1. No need for a separate tube sealer—CAPD patients can weld and "bag-off" with the same device.

2. The strength of the seal can be controlled so the user can "dial-in" the desired seal integrity.

3. Avoids use of RF fields—important on spacecraft or for the military.

4. User always has the option of welding the tube back together if he/she makes a mistake.

5. For those people who want absolute seal integrity, the weld function can be used to weld a presterilized, pre-sealed, stub end onto the tube.

FIGS. 1–4 illustrate an apparatus 10 for practicing one embodiment of this invention. As shown therein apparatus 10 is generally of the same structure and operation as the device of parent application Ser. No. 51,390. Apparatus 10 thus includes a pair of spaced tube holders 12,14 having two sets of tube receiving pockets or grooves 16,18 and 20,22. In the practice of this invention, however, only pockets 16 and 20 are used for receiving a tube T which spans the space between the tube holders. The remaining set of pockets 18,22 remains empty. Tube T may be fluid filled or dry.

Figure 1:
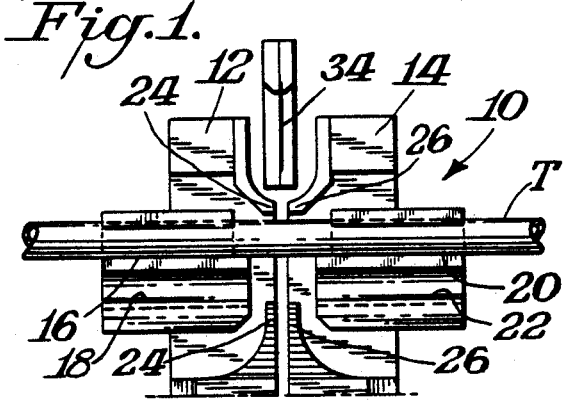
FIG. 1 is a top plan view of a portion of an apparatus for sealing the end of a tube in connection with this invention.
Figure 2:
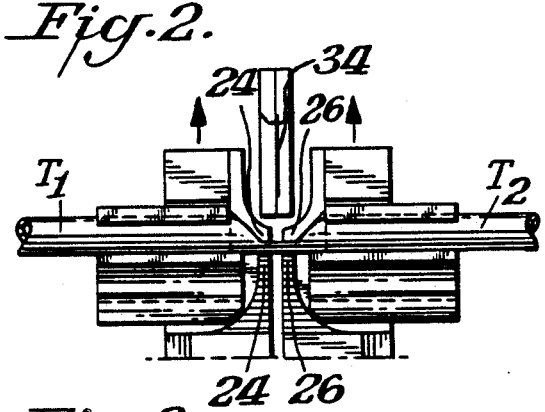
FIGS. 2-3 are top plan views similar to FIG. 1 showing different stages of operation.

FIG. 2 illustrates the next step in operation wherein clamping jaws 24,26 are moved toward each other to flatten tube T in the same manner as in parent application Ser. No. 51,390.

Figure 3:
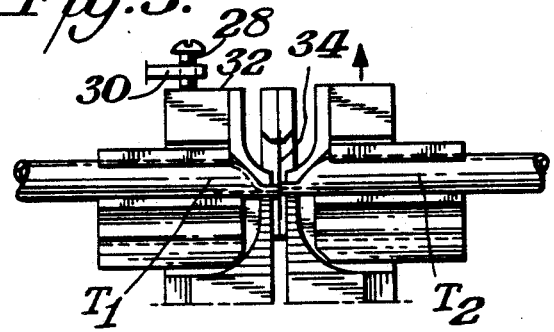
Figure 4:
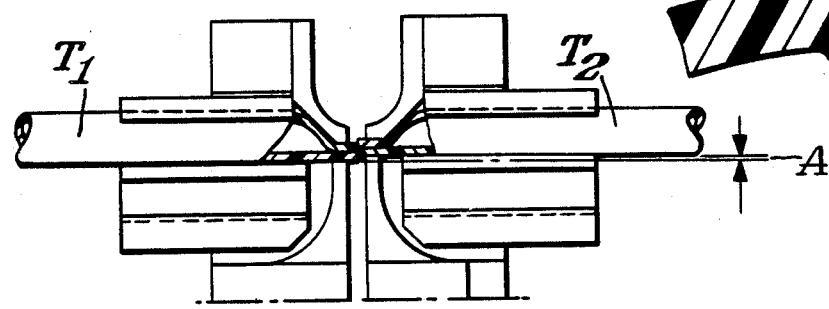
FIG. 4 is a top plan view similar to FIGS. 1-3, but partly in section showing the mis-aligned tube sections.

FIG. 3 shows the next step in the sequence of operation which includes a variation from the apparatus of the parent application. This variation includes the mounting of an adjustable stop 28 in the path of motion of tube holder 12. Adjustable stop 28 may take any suitable form such as a threaded bolt passing through a threaded bracket 30 so that its remote end 32 would limit the amount of movement of shifting of tube holder 12. In operation the carriage of device 10 moves the flattened tube T into the hot welding wafer 34 in the same manner as in the parent application. Unlike the parent application, however, as soon as the tube T is cut one of the tube clamp assemblies or tube holders 12 hit adjustable stop 28 and stops its motion with respect to the wafer 34. The other clamp holder 14 continues to move its half of the severed tube as if to perform the shift operation used in welding when practicing the invention of the parent application. See FIG. 3.

Figure 8:
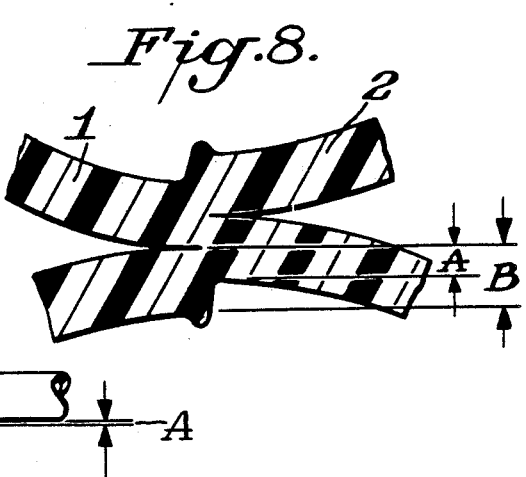
FIG. 8 is a cross-sectional view similar to FIGS. 5-7 showing a sealed tube in accordance with this invention.

The distance traveled by the tube holder or clamp assembly 14 may be controlled by an encoder and counter arrangement or any other suitable means. As soon as the tube holder 14 moves into mis-alignment of such tube section $T_1$ with respect to cut tube section $T_2$, the forward motion of the carriage is reversed and the tube sections $T_1$, $T_2$ begin to come off the wafer 34. In this embodiment of the invention the mis-alignment is the distance A which corresponds to about one-half of the tube wall thickness B (see also FIG. 8). The cycle then continues as in the welding operation of parent application Ser. No. 51,390 wherein the tube holders 12,14 are shifted toward each other to cause the melted ends of tube sections $T_1$, $T_2$ to be pushed together. In this respect, the tube sections $T_1$, $T_2$ are brought back to the dwell point on the edge of the wafer, then dwell at that location, then come off the wafer and then are pushed together. FIGS. 7 and 8 compare the tack seal produced by the welding operation of parent application Ser. No. 51,390 (FIG. 7) to the permanent seal in accordance with this invention (FIG. 8). The tack seal of FIG. 7 is extremely small and thus easily opened. The seal of FIG. 8, however, actually uses one of the tube walls of the tube sections from the mating tube as a patch to permanently weld the tube walls together. The degree of permanence would be continuously adjustable simply by adjusting the degree of mismatch of mis-alignment which in turn would be controlled by the manipulation of the adjustable stop 28.

FIGS. 9–11 show a variation of this invention which still utilizes a mis-alignment of the tube sections $T_1$, $T_2$ by the distance A which is about one-half of the tube wall thickness. The mis-alignment is achieved, however, by mounting the tube holders 36,38 in a pre-shifted condition whereby the tubes are flattened by the clamps on tube holders 36,38. The tube T is then severed with hot wafer 40 which also melts the ends of the resulting tube sections $T_1$, $T_2$. Alternatively, the tube T may be cut with a cold wafer and subsequently heated with any suitable heating means such as illustrated in FIG. 17. FIG. 9 illustrates the first step of operation wherein the tube is placed in the tube holders before the cutting takes place. FIG. 10 illustrates the severing or cutting operation and also shows the misalignment of the resulting tube sections $T_1$, $T_2$. FIG. 11 illustrates the next step in operation wherein the wafer 40 is removed and the molten tube ends are pressed together. This practice of the invention is characterized in that a tube shifting is not necessary since the tube holders 36,38 are rigidly fixed but in the pre-misaligned condition. The sealing takes place by the mis-alignment when the tube holders are moved toward each other.

FIGS. 12–15 illustrate a variation of this invention wherein the tube T is mounted in a pair of aligned tube holders 42,44 which clamp the tube at spaced location to flatten the tube as in the parent application. Tube T is severed by wafer 46 (FIGS. 13) which also melts the ends of the resulting tube sections $T_1$, $T_2$, as previously described.

FIG. 14 illustrates the next step in the sequence of operations wherein one tube section $T_2$ is shifted while the other tube section $T_1$ remain stationary so that the two severed ends are completely out of alignment with each other. Wafer 46 would then be removed from the operative area. As shown in FIG. 15 a cold die pocket 48,50 is located in line with each tube section $T_1$, $T_2$ when the tube sections are in their mis-aligned condition. The tube holders 42,44 are then shifted toward each other so that the end of each tube section $T_1$, $T_2$ is brought into contact with the cold die pocket so as to mold and cool the plastic material.

FIGS. 16–18 illustrate yet another embodiment of this invention where in the tube T is placed in a pair of tube holders 52,54 and the tube is clamped as previously described. In this embodiment of the invention a sharp knife 56 which may for example, be Teflon coated is pushed through the tube to sever the tube into the sections $T_1$, $T_2$. The knife may be heated to about 250°–310° F. to ease its passage through the pvc material (see FIG. 16).

FIG. 17 illustrates the next step in the sequence of operation wherein by means of a cam or any other suitable means the tube sections are caused to separate far enough that a radiant heater 58 can be positioned so as to heat the tube ends $T_1$, $T_2$ to effect a melting and if desired sterilizing of the two ends. Heater 58 is then removed and as shown in FIG. 18 a cold die block 60 is brought into place between the spaced tube sections $T_1$, $T_2$. Die block 60 includes a pair of die pockets 62,64. The molten tube ends are pushed into die pockets 62,64 to form and cool the tube seal. In this embodiment it is preferable that the knife, the radiant heater and the die block be mounted on a common carriage with the tube holders mounted to pivoting arms.

In the various embodiments the cutting and heating may be by a heated wafer or by a knife and separate heater.

As can be appreciated the present invention thus provides various techniques whereby a single tube may be effectively sealed after it has been used as a conduit.

What is claimed is:

1. A device for sealing the end of a thermoplastic tube comprising a pair of spaced apart tube holders having tube receiving pockets whereby a single tube may be placed in said pockets spanning the space therebetween, clamping means on said tube holders for clamping the tube closed at a pair of spaced locations, cutting means relatively movable into the space between said pockets to cut through the tube between said spaced locations to form two distinct tube sections, said cutting means being relatively movable out of said space between said pockets, means for melting the ends of the tube sections, means for moving said pockets out of alignment with each other by a distance corresponding to about one-half the thickness of the wall of the tube, means for moving said tube holders toward and away from each other, said means for moving said pockets out of alignment including a stop member in the path of motion of one of said tue holders to prevent said one of said tube holders from moving while the other of said tube holders continues to move, said stop member being positioned to cause said tube receiving pockets to be out of alignment, and means for completely sealing closed the end of at least one of the tube sections.

2. The device of claim 1 wherein said tube receiving pockets are moved out of alignment by a distance which is only a minor portion of the width of said pockets, and said means for completely sealing comprising said means for moving said tube holders toward and away from each other whereby the melted ends of the tube sections are pressed against each other with the wall of one tube section overlapping the wall of the other tube section.

3. The device of claim 2, in combination therewith, a tube, and said pockets being moved out of alignment by a distance corresponding to one-half the thickness of the wall of said tube.

4. The device of claim 1 wherein said stop member is adjustably mounted to adjust the amount said pockets are moved out of alignment.

5. The device of claim 1 wherein said pockets are moved out of alignment by a distance greater than the width of one of said pockets, and said means for completely sealing comprises a cold die pocket in line with one of said tube receiving pockets.

6. The device of claim 5 including a cold die pocket in line with each of said tube receiving pockets.

7. A device for sealing the end of a thermoplastic tube comprising a pair of spaced apart tube holders having tube receiving pockets whereby a single tube may be placed in said pockets spanning the space therebetween, clamping means on said tube holders for clamping the tube closed at a pair of spaced locations, cutting means relatively movable into the space between said pockets to cut through the tube between said spaced locations to form two distinct tube sections, said cutting means being relatively movable out of said space between said pockets, means for melting the ends of the tube sections, said tube holders being shiftable out of alignment with each other by a distance greater than the width of one of said tube receiving pockets, a cold die pocket in line with at least one of the tube sections after the ends of the tube sections have been melted, and means for moving said tube holder having the at least one of the tube sections toward said cold die pocket whereby the end of the at least one of the tube sections is completely sealed upon contacting said cold die pocket.

8. The device of claim 7 wherein a cold die pocket is provided for each of the tube sections.

9. A method for sealing the end of a thermoplastic tube comprising the steps of placing the tube in aligned pockets in a pair of spaced apart tube holders with the tube spanning the space between the tube holders, clamping the tube closed at two spaced locations with each location being at one of the tube holders, cutting through the tube at a location in the space between the tube holders and between the two clamped locations to form two tube sections severed from each other, heating the ends of the two tube sections to melt the ends, moving the tube holders and tube sections toward each other with the tube sections not completely contacting each other, and completely sealing closed at least one of the tube ends after the tube ends have been moved toward each other, wherein after the tube has been cut and its ends heated a cold die block is inserted between the heated ends, and the heated ends are brought into contact with a respective cold die pocket in the die block to perform the sealing step.

10. A method for sealing the end of a thermoplastic tube comprising the steps of placing the tube in pockets in a pair of spaced apart tube holders with the tube spanning the space between the tube holders, clamping the tube closed at two spaced locations with each location being at one of the tube holders, cutting through the tube at a location in the space between the tube holders and between the two clamped locations to form two tube sections severed from each other, heating the ends of the two tube sections to melt the ends, moving the tube holders and tube sections toward each other, locating the pockets out of alignment with each other before the tube ends are moved toward each other, and completely sealing closed at least one of the tube ends after the tube ends have been moved toward each other, wherein the tube pockets are initially aligned with each other and then moved out of alignment by a distance corresponding to about one-half the thickness of the wall of the tube, and the tube ends are brought into contact with each other in the misaligned position.

11. A method for sealing the end of a thermoplastic tube comprising the steps of placing the tube in pockets in a pair of spaced apart tube holders with the tube spanning the space between the tube holders, clamping the tube closed at two spaced locations with each location being at one of the tube holders, cutting through the tube at a location in the space between the tube holders and between the two clamped locations to form two tube sections severed from each other, heating the ends of the two tube sections to melt the ends, moving the tube holders and tube sections toward each other, locating the pockets out of alignment with each other before the tube ends are moved toward each other, and completely sealing closed at least one of the tube ends after the tube ends have been moved toward each other, wherein the tube pockets are initially misaligned by a distance corresponding to about one-half the thickness of the wall of the tube, and the tube ends are brought into contact with each other in the misaligned position.

12. A method for sealing the end of a thermoplastic tube comprising the steps of placing the tube in pockets in a pair of spaced apart tube holders with the tube spanning the space between the tube holders, clamping the tube closed at two spaced locations with each location being at one of the tube holders, cutting through the tube at a location in the space between the tube holders and between the two clamped locations to form two tube sections severed from each other, heating the ends of the two tube sections to melt the ends, moving the tube holders and tube sections toward each other with the tube sections not completely contacting each other, locating the pockets out of alignment with each other before the tube ends are moved toward each other, and completely sealing closed at least one of the tube ends after the tube ends have been moved toward each other, wherein the tube ends are out of alignment by a distance greater than the width of one of the pockets, and the at least one of tubes end is sealed by being brought into contact with a cold die pocket.

13. A device for sealing the end of a thermoplastic tube comprising a pair of spaced apart tube holders having tube receiving pockets whereby a single tube may be placed in said pockets spanning the space therebetween, clamping means on said tube holders for clamping the tube closed at a pair of spaced locations, cutting means relatively movable into the space between said pockets to cut through the tube between said spaced locations to form two distinct tube sections, said cutting means being relatively movable out of said space between said pockets, means for melting the ends of the tube sections, said tube holders being fixedly mounted with respect to each other in directions perpendicular to said tube receiving pockets with said pockets out of alignment with each other, means for moving said misaligned tube holders toward and away from each other, and means for completely sealing closed the end of at least one of tube sections.

14. The device of claim 13 wherein said tube receiving pockets are mounted out of alignment by a distance which is only a minor portion of the width of said pockets, and said means for completely sealing comprising said means for moving said tube holders whereby the melted ends of the tube sections are pressed against each other with the wall of one tube section overlapping the wall of the other tube section.

15. A device for sealing the ends of a thermoplastic tube comprising a pair of spaced apart tube holders having aligned tube receiving pockets whereby a single tube may be placed in said pockets spanning the space therebetween, clamping means on said tube holders for clamping the tube closed at a pair of spaced locations, cutting means relatively movable into the space between said pockets to cut through the tube between said spaced locations to form two distinct tube sections, said cutting means being relatively movable out of said space between said pockets, means for melting the ends of the tube sections, a die block having cold die pockets in opposite surfaces of said die block with said cold die pockets being fixedly aligned relative to each other and with each cold die pocket being alignable with a respective one of the tube sections after the ends of the tube sections have been melted, said die block being relatively movable into and out of said space between said tube receiving pockets, and means for moving said tube holders toward said cold die pockets whereby the ends of the tube sections are completely sealed upon contacting said cold die pockets.

* * * * *